United States Patent
Le Peltier et al.

(10) Patent No.: US 8,309,782 B2
(45) Date of Patent: Nov. 13, 2012

(54) PROCESS FOR DEHYDROGENATION IN THE PRESENCE OF A BIMETALLIC OR MULTI-METALLIC CATALYST THAT HAS AN OPTIMIZED BIMETALLICITY INDEX AND AN OPTIMIZED HYDROGEN ADSORPTION CAPACITY

(75) Inventors: Fabienne Le Peltier, Rueil Malmaison (FR); Sylvie Lacombe, Vernaison (FR); Christophe Chau, Rueil Malmaison (FR); Stephane Morin, Saint Genis Laval (FR); Lars Fischer, Vienne (FR); Renaud Revel, Serpaize (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 389 days.

(21) Appl. No.: 12/520,445

(22) PCT Filed: Dec. 7, 2007

(86) PCT No.: PCT/FR2007/002022
§ 371 (c)(1),
(2), (4) Date: Feb. 22, 2010

(87) PCT Pub. No.: WO2008/084147
PCT Pub. Date: Jul. 17, 2008

(65) Prior Publication Data
US 2010/0168493 A1    Jul. 1, 2010

(30) Foreign Application Priority Data
Dec. 22, 2006   (FR) ..................................... 06 11412

(51) Int. Cl.
*C07C 5/333* (2006.01)
(52) U.S. Cl. ........ 585/660; 585/654; 502/223; 502/226; 502/229; 502/230; 502/222; 208/139

(58) Field of Classification Search ................. 585/654, 585/660; 502/223, 226, 229, 230, 222, 231; 208/139
See application file for complete search history.

(56) References Cited

U.S. PATENT DOCUMENTS

| | | | |
|---|---|---|---|
| 3,531,543 A | 9/1970 | Clippinger et al. | |
| 3,892,657 A * | 7/1975 | Wilhelm | 208/139 |
| 4,677,237 A * | 6/1987 | Imai et al. | 585/660 |
| 4,786,625 A | 11/1988 | Imai et al. | |
| 6,600,082 B2 | 7/2003 | Le Peltier et al. | |

FOREIGN PATENT DOCUMENTS

| | | |
|---|---|---|
| EP | 0 248 130 | 12/1987 |
| EP | 0 568 303 | 11/1993 |
| EP | 1 182 180 | 2/2002 |

OTHER PUBLICATIONS

International Search Report for PCT/FR2007/002022 dated Jul. 7, 2008.

* cited by examiner

*Primary Examiner* — In Suk Bullock
*Assistant Examiner* — Sharon Pregler
(74) *Attorney, Agent, or Firm* — Millen, White, Zelano & Branigan, P.C.

(57) ABSTRACT

The invention relates to a process for dehydrogenation of a hydrocarbon feedstock in the presence of a catalyst that comprises a noble metal M that is selected from the group that consists of platinum, palladium, rhodium, and iridium, at least one promoter X1 that is selected from the group that consists of tin, germanium, and lead, and optionally a promoter X2 that is selected from the group that consists of gallium, indium and thallium, an alkaline or alkaline-earth compound and a porous substrate, in which the atomic ratio X1/M and optionally X2/M is between 0.3 and 8, the $H_{tr}/M$ ratio that is measured by hydrogen adsorption is greater than 0.40, and the bimetallicity index BMI that is measured by hydrogen/oxygen titration is greater than 108.

15 Claims, 1 Drawing Sheet

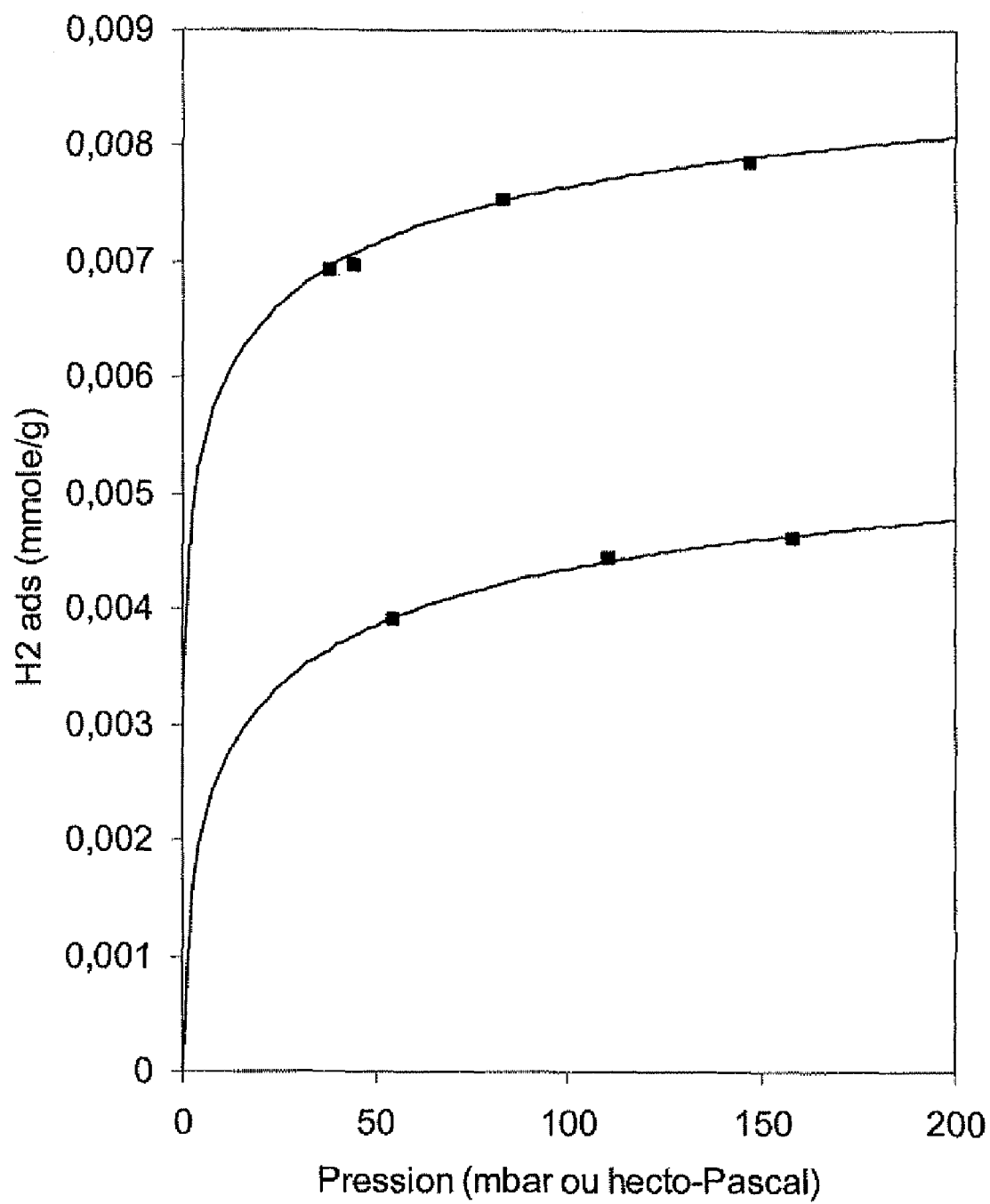

PROCESS FOR DEHYDROGENATION IN THE PRESENCE OF A BIMETALLIC OR MULTI-METALLIC CATALYST THAT HAS AN OPTIMIZED BIMETALLICITY INDEX AND AN OPTIMIZED HYDROGEN ADSORPTION CAPACITY

FIELD OF THE INVENTION

This invention relates to the domain of the dehydrogenation of hydrocarbon feedstocks in the presence of a bimetallic or multi-metallic catalyst based on a noble metal.

The dehydrogenation of the hydrocarbons is a process that makes it possible to synthesize numerous chemical products that are used as a base in the preparation of manufactured products such as gasolines with a high octane number, plastics, or plasticizers, detergents, synthetic rubbers, and various additives for plastics, lubricants or adhesives.

PRIOR ART

The prior art describes numerous catalysts based on noble metals from group VIII, alkalines and promoters. Nevertheless, these formulations can also be the object of development, making it possible to improve their performance levels, in particular for the purpose of reducing the secondary reactions—such as isomerization or cracking—even more, or obtaining more stable catalysts over time, or else promoting the conversion of molecules that are difficult to dehydrogenate.

U.S. Pat. No. 4,786,625 describes dehydrogenation catalysts that comprise a metal of the platinum group and a modifier element that is selected from the group that consists of tin, germanium, rhenium or mixtures thereof that are deposited on a refractory oxide, having a diameter of at least 850 microns in which the platinum is deposited on the surface of the substrate, and the modifier is impregnated uniformly in the substrate.

Patent Application US 2005/0033101 A1 describes a process for dehydrogenation in which the feedstock is brought into contact with a catalyst that comprises at least one noble metal from group VIII, an alkaline or an alkaline-earth, and a compound that is selected from among tin, germanium, lead, indium, gallium, thallium or the mixture thereof. These various components of catalysts are deposited on a substrate that is based on alumina and that comprises essentially theta-alumina.

The U.S. Pat. No. 6,600,082 B2 describes a process for dehydrogenation of organic compounds that use a catalyst that is based on metals of group VIII and tin, in which a portion of the tin is in a form that is reduced to the metallic state and the catalyst is in a partially oxidized state that is obtained in a controlled manner.

SUMMARY OF THE INVENTION

The invention relates to a process for dehydrogenation of a hydrocarbon feedstock in the presence of a catalyst that comprises a noble metal M that is selected from the group that consists of platinum, palladium, rhodium and iridium, at least one promoter X1 that is selected from the group that consists of tin, germanium, and lead, and optionally at least one promoter X2 that is selected from the group that consists of gallium, indium and thallium, an alkaline or alkaline earth compound, and a porous substrate, in which the X1/M atomic ratio—and optionally the X2/M atomic ratio—is between 0.3 and 8, the $H_{tr}/M$ ratio that is measured by hydrogen adsorption is greater than 0.40, and the bimetallicity index BMI that is measured by hydrogen/oxygen titration is greater than 108.

DETAILED DESCRIPTION OF THE INVENTION

This invention relates to a process for dehydrogenation of a hydrocarbon feedstock in the presence of a catalyst that comprises a noble metal M that is selected from the group that consists of platinum, palladium, rhodium, and iridium, at least one promoter X1 that is selected from the group that consists of tin, germanium, and lead, an alkaline or alkaline-earth compound, and a porous substrate, in which the X1/M ratio is between 0.3 and 8.

In the catalyst according to the invention, the X1/M atomic ratio is preferably between 0.6 and 6, more preferably between 0.7 and 5, more preferably between 0.8 and 4, also very preferably between 1.2 and 2.9, and even between 1.4 and 2.5.

The catalyst according to the invention can also optionally comprise at least one promoter X2 that is selected from the group that consists of gallium, indium and thallium. Preferably, the X2/M ratio is then between 0.3 and 8, more preferably between 0.6 and 6, even more preferably between 0.7 and 5, much more preferably between 0.8 and 4, very preferably between 1.0 and 2.9, and even between 1.2 and 2.6.

The catalyst according to the invention preferably contains 0.01 to 10% by weight, more preferably 0.02 to 2% by weight, and very preferably 0.05 to 0.5% by weight of at least one noble metal M that is selected from the group that consists of platinum, palladium, rhodium, and iridium. Preferably, the metal M is platinum or palladium, and very preferably platinum. According to a preferred variant of the process according to the invention, the catalyst can advantageously contain both platinum and iridium.

The content of promoter X1 or X2 is preferably between 0.005 to 10% by weight and more preferably between 0.01 and 5% by weight, and very preferably between 0.1 and 2% by weight.

According to a variant of the process according to the invention, the promoter X1 is selected from among tin and germanium. Preferably, the promoter X2 is indium. The catalyst according to the invention can therefore comprise two promoters such as, for example, tin and indium or germanium and indium or tin and gallium, or 3 promoters such as tin and germanium and indium or else tin and gallium and indium. Very preferably, these are then tin and indium.

According to another variant, the catalyst according to the invention can therefore comprise only one promoter X1, and preferably X1 is tin.

According to another variant, the catalyst according to the invention can comprise both a promoter X1 and a promoter X2, and preferably X1 is tin and X2 is indium.

The alkaline compound is preferably selected from the group that consists of: lithium, sodium, potassium, rubidium and cesium. Lithium, sodium and potassium are very preferred alkalines, and lithium or potassium are even more preferred alkalines.

The alkaline compound content is preferably between 0.05 and 10% by weight, more preferably between 0.1 and 5% by weight, and even more preferably between 0.15 and 2% by weight.

The alkaline-earth compound is preferably selected from the group that consists of: magnesium, calcium, strontium or barium. Magnesium or calcium are very preferred alkaline-earths, and magnesium is the most preferred alkaline-earth. The alkaline-earth compound content is preferably between 0.05 and 10% by weight, more preferably between 0.1 and 5% by weight, and even more preferably between 0.15 and 2% by weight.

Furthermore, the catalyst according to the invention has a hydrogen adsorption capacity such that the ratio between the irreversibly adsorbed hydrogen quantity and the metal of the platinum group (also called $H_{ir}/M$ atomic ratio) is greater than 0.4, preferably greater than 0.43, more preferably between 0.43 and 0.9, even more preferably between 0.45 and 0.65, and very preferably between 0.45 and 0.6.

Measurement of the $H_{ir}/M$ Ratio

The $H_{ir}/M$ ratio of a catalyst according to the invention can be determined by means of the hydrogen chemisorption technique. This technique is known to one skilled in the art and is described in, for example, Chapter 5, page 127 ff of the survey book entitled: "Catalytic Naphtha Reforming, Science and Technology, by G. J. Antos, A. M. Aitani and J. M. Parera, Editor Marcel Decker, 1995. It actually makes it possible to characterize complex systems based on platinum or other metals and one or more promoters.

Various protocols have been proposed in the literature to determine the quantities of chemisorbed hydrogen. Hydrogen can be chemisorbed by a metal catalyst in a reversible or irreversible manner. The detailed protocol presented below is preferred for the determination of the $H_{ir}/M$ ratio according to the invention that causes the chemisorbed hydrogen quantity $H_{ir}$ to occur in an irreversible way.

Protocol for Treatment of the Sample:
 a) Calcination under a flow of dry air for 2 hours at 500° C.
 b) Transfer of air at ambient temperature for charging into the volumetric measuring cell in less than 10 minutes.
 c) Reduction in the cell with increase in temperature by 20° C. to 450° C. in 1 hour, holding at 450° C. for 4 hours under a hydrogen flow (50 ml min$^{-1}$), return to 25° C. under hydrogen, then sealing of the air vent of the cell.

Adsorption Measurements:

The apparatus that is used is a static volumetric analysis apparatus.
 a) Desorption under dynamic vacuum (10$^{-5}$ mbar or 1 mPa) at 350° C., for 3 hours then return to 25° C. under vacuum.
 b) Measurement of the adsorbed hydrogen quantity at 25° C. under a given hydrogen pressure, after adsorption for 60 minutes.

The phases a) and b) are reproduced so as to trace the adsorption isotherm between about 40 and 300 mbar (4 to 30 kPa).

Two measurements are made in desorbent under vacuum at 25° C. for 3 hours that make it possible to measure the adsorbed hydrogen quantity in a reversible manner.

FIG. 1 shows an isotherm example obtained for a catalyst according to the invention. The curve of the bottom corresponds to the reversible adsorption isotherm and the curve of the top shows the total adsorption isotherm.

It is possible to establish a model of the adsorption isotherm by allowing a dissociative adsorption of hydrogen on platinum, according to the Langmuir equation, with an irreversible portion $H_{ir}$ at 25° C. and a reversible portion $H_{rev}$.

The total quantity of adsorbed hydrogen is defined by the equation (I) below:

$$Q_{ads} = H_{ir} + H_{rev}(K_1 \cdot P)^{0.5}/(1+(K_1 \cdot P)^{0.5}) \quad \text{(I)}$$

where P is the pressure that is expressed in mbar (or hectopascal), and $K_1$ is the Langmuir constant. The establishment of a model of the adsorption isotherm therefore makes it possible to determine the parameter $H_{ir}$.

Bimetallicity Index:

The optimized catalyst according to the invention has a bimetallicity index (BMI) that is greater than 108. This index that is defined below is measured by the detailed hydrogen/oxygen titration technique that is presented below. Preferably, this BMI index is greater than 110 and very preferably greater than 115, and even 120. Furthermore, according to a very preferred variant, this index is less than 170 and even more preferably less than 160. Furthermore, it is possible according to another preferred variant that this index is between 108 and 160, or very preferably between 110 and 160, and even between 110 and 150, or else between 115 and 145.

The bimetallicity index (BMI) is determined by using the hydrogen-oxygen titration technique in a special way. This technique is known to one skilled in the art for determining the dispersion of a metal, i.e., the ratio of the number of surface atoms of one metal to the total number of atoms of this same metal. It is described in, for example, Chapter 5, pages 130 and 131 of the survey book entitled "Catalytic Naphtha Reforming, Science and Technology," by G. J. Antos, A. M. Aitani and J. M. Parera, Editor Marcel Decker, 1995. It consists in chemisorbing oxygen on a metal M that is contained in a previously reduced catalyst and therefore containing a chemisorbed hydrogen layer. The stoichiometric reaction that shows the titration stage of the hydrogen that is chemisorbed by oxygen is considered as being the following:

$$M-H + \tfrac{3}{4}O_2 \rightarrow M-O + \tfrac{1}{2}H_2O$$

The quantity of oxygen consumed during titration makes it possible to determine the quantity of accessible metal sites. In the case of a supported Pt—Sn bimetallic system, it was shown, for example by Sharma et al. in Applied Catalysis A 168 (1998) 251, that by operating two successive oxygen titration cycles, the quantity of oxygen adsorbed during the first cycle was more significant than the one adsorbed during the second cycle. This is explained by the fact that during the first cycle, the reduction of tin contributes to the consumption of oxygen, whereas the second cycle essentially reflects the chemisorption of oxygen on the accessible platinum sites.

This second cycle can be used to determine the dispersion of the metal M. In the catalyst according to the invention, the dispersion of the metal M is preferably greater than 80%, more preferably greater than 90%, and very preferably greater than 95%.

The bimetallicity index called "BMI" that is used as a criterion in this invention is calculated from the volume of oxygen that is consumed during the first hydrogen-oxygen titration. It is calculated as follows:

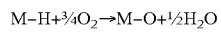

$$BMI = (V1/24041) * 4/3/(0.01 T_M/MM)$$

with
 V1: Volume of oxygen consumed during the first titration at 20° C. on the previously reduced catalyst, expressed in cm$^3$ per gram of catalyst.
 $T_M$: Metal content of the platinum group in the catalyst, expressed in % by weight
 MM: Molar mass of the metal of the platinum group The bimetallicity index reflects the degree of interaction of the metal of the platinum group with any promoter that is present in the catalyst. The preferred experimental protocol of hydrogen-oxygen titration for the determination of the bimetallicity index is as follows:
 a) Calcination of 2 grams of catalyst under a dry air flow (20 ml/minute) with a flow rate of 1 Nl/(g·h) for 2 hours at 500° C.,
 b) Return to 20° C. under dry air,
 c) Purging by an inert gas (20 ml/minute), preferably helium with a purity of more than 99.999%, d) Transfer under hydrogen (20 ml/minute), preferably with a purity of more than 99.999% and reduction at 500° C. for 2 hours
e) Return to 20° C.
f) Purging by an inert gas (20 ml/minute), preferably helium with a purity of more than 99.999%,
g) Oxygen pulses with a volume of 0.27 $cm^3$, preferably with a purity of greater than 99.995%, and purified by means of one or more molecular sieves (sieve 3A, 4A or 13×) at 20° C. until there is no longer oxygen consumption or after at least 10 pulses of constant surface area.

The volume of oxygen consumed during stage g) is used for the calculation of the bimetallicity index.

Substrate of the Catalyst According to the Invention:

The porous substrate that is used in the catalyst according to the invention is generally a refractory oxide that is selected from among the oxides of magnesium, titanium, zirconium, alumina, silicon or mixture thereof. Preferably, it is silica, alumina or silica-alumina, and very preferably alumina.

In the case of the catalysts according to the invention that are used in a dehydrogenation process, the porous substrate in addition can be selected from among the zeolites and molecular sieves or mixtures of zeolites or molecular sieves with one of the refractory oxides cited above, and preferably selected from among the following catalyst substrates: zeolite X, zeolite Y, modenite, faujasite, ZSM-5, ZSM-4, ZSM-8, EUO, and mazzite.

According to the invention, said porous substrate advantageously comes in the form of balls, extrudates, pellets, powder, or irregular and non-spherical agglomerates whose specific shape may result from a crushing stage. Very advantageously, said substrate comes in the form of balls or extrudates or agglomerates. The porous volume of the substrate is preferably between 0.1 and 1.5 $cm^3/g$, more preferably between 0.4 and 1.2 $cm^3/g$. Furthermore, said porous substrate has a specific surface area advantageously of between 50 and 600 $m^2/g$, preferably between 70 and 250 $m^2/g$, and even between 80 and 200 $m^2/g$.

Preparation of the Catalyst:

It was discovered by the applicant that the catalysts according to the invention were obtained in particular by depositing the promoter X1 twice (two separate stages), a first stage before the introduction of the element of the platinum group, and a second stage after the introduction of the element of the platinum group.

The process for preparation of the catalyst according to the invention generally comprises the following stages:
a) Introduction of the promoter X1 in the substrate or on the substrate,
b) Optional drying stage of the product that is obtained at the end of stage a,
c) Calcination of the product that is obtained in stage a or optionally in stage b at a temperature that is preferably between 350 and 650° C.,
d) Deposition of at least one metal of the platinum group M,
e) Optional drying under neutral atmosphere or atmosphere containing oxygen, at a moderate temperature that preferably does not exceed 150° C.,
f) Deposition of a complementary fraction of the promoter X1 on the product that is obtained in stage d or e,
g) Optional drying of the product that is obtained in stage f,
h) Calcination of the product that is obtained in stage f or g; this calcination is preferably conducted in the presence of air, and this air can also be enriched with oxygen or nitrogen.

More specifically, for the first stage (stage a) for introducing the promoter X1 (used by itself or in a mixture), X1 can be incorporated in the substrate, for example during the synthesis of the substrate or during the shaping of the substrate. X1 can also be introduced onto the substrate, for example by impregnation of the previously shaped substrate. X1 can also be introduced partially during the synthesis or shaping of the substrate and partially by deposition on the shaped substrate. 30% to 70% by weight, preferably 40% to 65% by weight, and even more preferably 50% to 65% by weight, of the total quantity of X1 that is part of the composition of the catalyst according to the invention is thus introduced into the substrate or deposited on the substrate during this first introduction stage.

The X1 fraction that is introduced during the synthesis of the substrate is incorporated by any technique that is known to one skilled in the art. Without being exhaustive, the techniques for addition before or during the dissolution of the oxide precursors of the substrate, with or without curing, may be suitable. The introduction can therefore be done at the same time as or after the mixing of the precursors of the substrate.

According to a variant of the method for preparation according to the invention, the promoter X1 is introduced during the synthesis of the substrate according to a sol-gel-type technique. According to another variant, the promoter X1 is added to an alumina sol.

According to a third variant implementation of the invention, the promoter X1 is introduced during the shaping of the substrate according to the techniques of the prior art for shaping the substrate such as the procedures for shaping by extrusion or by the drop (oil-drop according to English terminology) coagulation.

In the case where the X1 fraction is deposited on the substrate, after its shaping, it can be impregnated by means of any technique that is known to one skilled in the art, and preferably by impregnation of a solution that contains one or more precursors of X1. The impregnation can be carried out by excess solution or else under dry conditions (the volume of solution containing X1 corresponding to the pore volume of the substrate). The impregnation can be carried out in the presence of radicals acting on the interaction between the precursor of the promoter X1 and the substrate. These radicals can be, for example, and without being limiting, mineral acids (HCl, NHO3) or organic acids (carboxylic acid types or polycarboxylic acid types), and complexing-type organic compounds, as is described in, for example, the U.S. Pat. No. 6,872,300 B1 and U.S. Pat. No. 6,291,394 B1. Preferably, the impregnation is carried out according to any technique that is known to one skilled in the art, making it possible to obtain a homogeneous distribution of the promoter X1 within the catalyst.

The precursors of the promoter X1 can be minerals or of organometallic type, optionally of water-soluble organometallic type. X1 is preferably selected from among the elements germanium and tin. The precursors that contain germanium can be selected from among at least one of the following reagents, without being exhaustive: oxides, tetra-alkoxides and fluorides of germanium. One example of an organo-soluble organometallic compound is the oxide $(EtGeO)_2O$. In the case of tin, various precursors can be used, alone or in a mixture. In particular, tin can be selected and, in a non-limiting way, in the group that is formed by the halogenated compounds, hydroxides, carbonates, carboxylates, sulfates, tartrates and nitrates. These forms of the tin can be introduced into the medium of preparation of the catalyst as is or generated in situ (for example, by introduction of tin and carboxylic acid). The tin-based precursors of organometallic type can be, for example, SnR4, where R represents an alkyl group, for example the butyl group, $Me_3SnCl$, $Me_2SnCl_2$, $Et_3SnCl$, $Et_2SnCl_2$, $EtSnCl_3$, $iPrSnCl_2$, and the hydroxides $Me_3SnOH$, $Me_2Sn(OH)_2$, $Et_3SnOH$, $Et_2Sn(OH)_2$, the oxides $(Bu_3Sn)_2O$, and the acetate $Bu_3SnOC(O)Me$. Preferably, the halogenated, in particular chlorinated, tin radicals will be used. In particular, $SnCl_2$ or $SnCl_4$ will be used advantageously.

Regardless of the variant that is used for the introduction of a fraction of the promoter X1 during stage a, it may be preferred to carry out a drying of the substrate (stage b) at the end after the promoter is added. This drying can be carried out according to any technique that is known to one skilled in the art, for example at a temperature of between 40° C. and 200° C., preferably between 80° C. and 180° C. This drying can be carried out with a programming of temperature and optionally can comprise temperature stages.

Whereby the promoter X1 has been introduced in the substrate or on the previously formed substrate, the protocol for preparation of the catalysts according to the invention generally requires a calcination before the deposit of the metal M of the platinum group (stage c). This calcination is preferably conducted at a temperature of between 350 and 650° C. and preferably between 400 and 600° C., and even more preferably between 400 and 550° C. The rise in temperature can be uniform or can include intermediate temperature stages, whereby these stages are reached with fixed or variable rates of temperature increase. These increases in temperatures can therefore be identical or can differ by their rate (by degree per minute or per hour). The gas atmosphere that is used during the calcination contains oxygen, preferably between 2 and 50%, and more preferably between 5 and 25%. Air can therefore also be used during this calcination stage.

After obtaining the substrate that contains an X1 fraction relative to the final composition of the catalyst, a deposit of metal from the platinum group M is made (stage d). In this stage, the metal M can be introduced by dry impregnation or excess solution, by using a precursor or a mixture of precursors containing a metal from the platinum group. The impregnation can be carried out in the presence of radicals that act on the interaction between the precursor of the metal M and the substrate. These radicals can be, without being limiting, mineral acids (HCl, $HNO_3$) or organic acids (carboxylic acid or polycarboxylic acid types), and complexing-type organic compounds. Preferably, the impregnation is carried out according to any technique that is known to one skilled in the art that makes it possible to obtain a homogeneous distribution of the metal M within the catalyst.

The precursors of the metal M are part of the following group, without this list being limiting: hexachloroplatinic acid, bromoplatinic acid, ammonium chloroplatinate, platinum chlorides, platinum dichlorocarbonyl dichloride, and tetraamine platinum chloride.

At this stage, the substrate that contains X1 (a fraction of the targeted total quantity of X1 in the final catalyst) and platinum is optionally dried (stage e), under neutral atmosphere or containing oxygen (with the air that can be used), at a moderate temperature and preferably not exceeding 150° C. Preferably, the drying is implemented at a temperature of less than 100° C. and over a period of several minutes to several hours.

At the end of this possible drying stage, a complementary fraction of the promoter X1 is deposited on the product that is obtained in stage d or e (stage f). More specifically, for the introduction of the radical X1 (used by itself or in a mixture) regarding this stage, 30% at least and 70% at most, and preferably 35% at least and 60% at most, and even 35% at least and 50% at most, of the total quantity of X1 entering into the composition of the catalyst according to the invention is thus introduced during this second stage for introduction of X1. The complementary fraction of the promoter X1 is deposited by bringing into contact a solution that contains the precursor.

In this stage, and in the case of the tin precursors, the tin tetrachloride SnCl4 will be used exclusively. In the case of the germanium precursors, the germanium tetrachloride GeCl4 will be used exclusively.

An optional drying of the product that is obtained in stage f can then be performed (stage g), under neutral atmosphere or containing oxygen (with the air that can be used), at a moderate temperature.

This stage is then generally followed by a calcination of the product that is obtained in stage f or g (stage h). This calcination is preferably conducted in the presence of air. This air can also be enriched with oxygen or nitrogen. Preferably, the oxygen content of this gas reaches 0.5 to 30% and even more preferably 2 to 25%.

This calcination is conducted at a temperature that occurs between 350 and 600° C. and preferably between 400 and 550° C., and even more preferably between 450 and 550° C. The temperature slope should be uniform and adequately fast. It can optionally contain temperature stages starting at 350° C. The rate of temperature increase is preferably greater than or equal to 5° C./minute. This rate of increase can be greater than 10° C./minute. Preferably, this temperature increase rate will not be less than 2° C./minute.

The optional promoter X2 can be introduced at one or more stages of the preparation of the catalyst. It can be introduced, for example, before, during or after the first stage for introduction of X1 (stage a, during the shaping of the substrate or by deposition on the substrate), by itself or in a mixture. X2 can also be introduced between the calcination stage of the substrate (stage c) and the introduction stage of the metal of the platinum group (stage d). Another possibility for introducing X2 is to incorporate it before the addition of the second X1 fraction (stage f); it can finally be introduced before the final calcination stage (stage h). The promoter X2 can be introduced once or several times, provided that it complies with the introduction conditions cited above. The promoter X2 can also be introduced by impregnation during an additional stage (stage i) that is located after stage h; stage i is then generally followed by stages j and k respectively for drying and calcination of the catalyst under the detailed conditions presented above for the stages for drying e or g or for calcination h.

In the case where a promoter X2 is present, the preparation process according to the invention can therefore also and advantageously comprise an additional stage for introduction of a promoter X2 that is located before stage a, or between stage c and stage d, or just before stage f or stage h, or else after stage h.

The optional promoter X2 can be introduced by means of any technique that is known to one skilled in the art. The ionic exchanges, dry impregnations or excess solution impregnations are suitable when it is a matter of deposition on the substrate (modified by X1 or not). In the case of incorporation during the preparation of the substrate, the promoter X2 can be added by mixing, co-precipitation, or dissolution without being limiting. In the case of gallium, indium, and thallium, nitrates or halides can be used. Regarding indium, precursors, by themselves or in a mixture, of nitrate, chlorides or bromides of indium are suitable. Other precursors can also be used.

On one sample of the catalyst that contains the metal M and the promoter X1 or the promoters X1 and X2, the bimetallicity index and the hydrogen chemisorption $H_{ir}/Pt$ ratio are determined after the "final" calcination described above and after a possible dehalogenation and before the deposition of an alkaline metal or an alkaline-earth metal that are described below.

The portion of the catalyst that is not used for these characterizations is subjected to an optional dehalogenation (stage m) and to a deposition of an alkaline or alkaline-earth metal (stage n).

If the deposition of the metals M and X has been carried out by introducing halogenated compounds, it is possible to initiate dehalogenation (stage m) whose operating conditions can be selected from among all of the methods that are known to one skilled in the art. It is possible to extract halogen in the liquid phase or in the gaseous phase. Preferably, the extraction of halogen is done in the gaseous phase in the presence of an oxygen fraction that exceeds 2% by volume, at temperatures of between 300° C. and 600° C., and even 400 to 550° C. Even more preferably, the gaseous phase is saturated with an aqueous phase that can contain a basic compound, such as ammonia or amines. The duration of the treatment is generally several hours; it is adjusted so as to obtain a final halogen content of between 100 ppm by weight and 5,000 ppm by weight, preferably between 200 and 2,000 ppm by weight, and even between 300 and 1,000 ppm by weight.

Below, the alkaline or alkaline-earth can be introduced (stage n) by means of any technique that is known to one skilled in the art. The ionic exchanges, dry impregnations or excess solution impregnations are suitable. Various precursors can be selected, by themselves or in a mixture, in a non-limiting way, in the group that is formed by the following compounds: hydroxides, carbonates, carboxylates, sulfates, tartrates and nitrates. Preferably, the impregnation is carried out according to any known technique of one skilled in the art that makes it possible to obtain a homogeneous distribution of the alkaline or alkaline-earth within the catalyst.

An optional drying can occur later, under neutral atmosphere or containing oxygen (from the air that can be used), at a moderate temperature. This stage is then followed by a last calcination. This calcination is conducted in the presence of air. This air can also be enriched with oxygen or nitrogen. Preferably, the oxygen content of this gas reaches 0.5 to 30% and even more preferably 2 to 25%. This calcination is conducted at a temperature that occurs between 350 and 600° C. and preferably between 380 and 550° C. and even more preferably between 430 and 550° C.

Implementation in a Dehydrogenation Process:

The catalyst according to the invention can be used in dehydrogenation processes. The processes for dehydrogenation of light paraffins make it possible to upgrade aliphatic hydrocarbons with a low boiling point, such as, for example, butanes and isobutanes, or pentanes and isopentanes that can be recovered after extraction of the unsaturated compounds from the steam-cracking or catalytic cracking fractions. The process for dehydrogenation of longer paraffins generally in the C8-C16 range is a significant commercial process because of the current demand for mono-olefins for the preparation of biodegradable detergents or pharmaceutical products.

The various processes for dehydrogenation of paraffins and naphthenes are differentiated by the selection of operating conditions and the composition of the feedstock. The adjustment of the operating conditions, based on the nature of the feedstock to be treated, is carried out so as to obtain the best suitability between pressure, temperature, yield, selectivity, stability and activity. This suitability can be obtained by means that are known to one skilled in the art.

The dehydrogenation reaction of the paraffins is generally operated at a pressure of between 0.02 and 2 MPa, preferably between 0.1 and 1 MPa, and at a temperature of between 400 and 800° C. based on the nature of the feedstock. The temperature is advantageously between 400 and 550° C. for a feedstock that essentially comprises isopentane. The temperature is advantageously between 450 and 550° C. for a feedstock that primarily comprises paraffins that comprise 9 to 22 carbon atoms per molecule. The feedstock can also contain unsaturated hydrocarbons that comprise 3 to 22 carbon atoms per molecule.

The mass rate of the feedstock treated by unit of mass of catalyst is generally between 0.5 and 200 $kg/(kg_{cat} \cdot h)$. It may be advantageous to use hydrogen as a diluent. The hydrogen/hydrocarbon molar ratio is generally between 0 and 20, preferably between 0.5 and 10.

The reaction for dehydrogenation of naphthenes is generally operated at a pressure of between 0.1 and 2 MPa, preferably between 0.1 and 1 MPa, and at a temperature of between 200 and 400° C. based on the nature of the feedstock. The mass rate of the feedstock that is treated per unit of mass of catalyst is generally between 0.5 and 100 $kg/(kg_{cat} \cdot h)$, preferably between 5 and 80 $kg/(kg_{cat} \cdot h)$.

The following examples illustrate the invention.

EXAMPLE 1

(Invention): Preparation of the Catalyst A SnPtSnK/A/203

An alumina ball substrate with a mean diameter of 1.2 mm is prepared by granulation of a boehmite powder, itself synthesized by neutralization of aluminum nitrate by soda with pH=10 at 70° C. After filtration and washing of the boehmite cake, the latter is dried at 100° C. for 3 hours. The boehmite is shaped by the simultaneous injection on a granulator plate of boehmite and acidified water. The balls that are thus obtained are then dried at 120° C. for 5 hours, and then calcined at 800° C. for 4 hours. The BET surface area, determined by nitrogen adsorption, of this substrate is then 134 $m^2/g$. The pore volume that is determined by mercury porosimetry is 0.86 $cm^3/g$.

A catalyst A is prepared on this substrate by depositing 0.3% by weight of platinum, 0.4% by weight of tin, 500 ppm by weight of chlorine, and 2% by weight of potassium.

400 $cm^3$ of an aqueous solution that contains tin dichloride is added to 100 g of alumina substrate in the presence of hydrochloric acid. It is left in contact for 3 hours, filtered, dried at 120° C., and then calcined for 2 hours at 500° C. at an air flow rate of 100 liters per hour. The quantity of tin dichloride is selected so as to obtain 0.2% by weight of tin on the calcined product. The solid is then brought into contact with 500 $cm^3$ of an aqueous solution of hexachloroplatinic acid and hydrochloric acid. It is left in contact for 4 hours, and then it is spin-dried. It is dried at 90° C., and then it is brought into contact with 400 $cm^3$ of an aqueous solution that contains tin tetrachloride in the presence of hydrochloric acid. It is left in contact for 4 hours, filtered, dried at 120° C., and then calcined for 2 hours at 500° C. at an air flow rate of 200 liters per hour, with a temperature increase rate of 7° C. per minute. The quantity of tin tetrachloride is selected so as to obtain a total of 0.4% by weight of tin on the final calcined catalyst.

The bimetallicity index and the $H_{ir}/Pt$ ratio are determined according to the methods that are described in the specification of the invention.

The remainder of the product is subjected to a dechlorination at 540° C. under saturated air with an aqueous solution of concentrated ammonia. The duration of this treatment is adjusted so as to obtain 500 ppm by weight of chlorine on the final catalyst. Below, it is brought into contact with 500 cm³ of an aqueous solution of potassium nitrate for 4 hours so as to obtain 2% by weight of potassium on the final catalyst, filtered, dried at 120° C., and then calcined for 2 hours at 500° C. at an air flow rate of 100 liters per hour.

EXAMPLE 2

(Invention): Preparation of the Catalyst B
SnPtSnK/A/203

A catalyst B is prepared according to the operating mode that is described in Example 1 by this time selecting the quantity of tin dichloride so as to obtain 0.27% by weight of tin on the calcined intermediate product, and the quantity of tin tetrachloride to be added so as always to obtain 0.4% tin on the final catalyst.

EXAMPLE 3

(For Comparison): Preparation of the Catalyst C
SnPtSnK/A/203

A catalyst C is prepared on the same substrate and with the same contents of tin, platinum, chlorine and potassium as in Example 1.

400 cm³ of an aqueous solution that contains tin dichloride is added to 100 g of alumina substrate in the presence of hydrochloric acid. It is left in contact for 4 hours, filtered, dried at 120° C., and then it is calcined for 2 hours at 500° C. at an air flow rate of 100 liters per hour. The quantity of tin dichloride that is introduced in a single stage is selected so as to obtain 0.4% by weight of tin on the final calcined product. The solid is then brought into contact with 400 cm³ of an aqueous solution of hexachloroplatinic acid and hydrochloric acid. It is left in contact for 4 hours, and then it is spin-dried. It is dried at 120° C., and then it is calcined for 2 hours at 500° C. at an air flow rate of 100 liters per hour, with a temperature increase rate of 7° C. per minute.

The determination of the bimetallicity index and the $H_{ir}$/Pt ratio, as well as the dechlorination, the deposition of the potassium and the final calcination are done as described in Example 1.

EXAMPLE 4

(For Comparison): Preparation of a Catalyst D
SnPtSnK/A/203

A catalyst C is prepared according to the operating method that is described in Example 1, with the sole difference being that during the two tin impregnations, the precursor that is used is an aqueous solution that contains tin dichloride in the presence of hydrochloric acid.

EXAMPLE 5

(Invention): Preparation of the Catalyst E
SnPtInSnK/A/203

A catalyst E is prepared on the same substrate as in Example 1 by depositing 0.3% by weight of platinum, 0.4% by weight of tin, 0.2% by weight of indium, 500 ppm by weight of chlorine, and 2% by weight of potassium.

400 cm³ of an aqueous solution that contains tin dichloride is added to 100 g of alumina substrate in the presence of hydrochloric acid. It is left in contact for 4 hours, filtered, dried at 120° C., and then calcined for 2 hours at 500° C. at an air flow rate of 100 liters per hour. The quantity of tin dichloride is selected so as to obtain 0.2% by weight of tin on the calcined product. The solid is then brought into contact with 400 cm³ of an aqueous solution of hexachloroplatinic acid and hydrochloric acid. It is left in contact for 4 hours and then spin-dried. It is dried at 90° C., and then it is brought into contact with 300 cm³ of an aqueous solution that contains indium nitrate in the presence of hydrochloric acid. Again, it is left in contact for 4 hours, spin-dried, dried, and then it is brought into contact with 200 cm³ of an aqueous solution that contains tin tetrachloride in the presence of hydrochloric acid. It is left in contact for 4 hours, spin-dried, dried at 120° C., and then it is calcined for 2 hours at 500° C. at an air flow rate of 100 liters per hour, with a temperature increase rate of 7° C. per minute. The quantity of tin tetrachloride is selected so as to obtain 0.4% by weight of tin in all on the calcined product.

The determination of the bimetallicity index and the $H_{ir}$/Pt ratio, as well as the dechlorination, the deposition of potassium and the final calcination are done as described in Example 1.

EXAMPLE 6

(Invention): Preparation of the Catalyst F
PtSnK/(Al2O3-Sn—In)

An alumina ball substrate, containing 0.2% by weight of tin and 0.2% by weight of indium, with a mean diameter of 1.2 mm, having a BET surface area of 130 m2/g, is prepared by granulation of the boehmite powder whose synthesis is described in Example 1 in the presence of acidified water, indium nitrate, and Et2Sn(OH)2. The balls that are thus obtained are then dried at 120° C. for 5 hours, and then calcined at 800° C. for 4 hours. The BET surface area, determined by nitrogen adsorption, of this substrate is then 130 m²/g. The pore volume that is determined by mercury porosimetry is 0.88 cm³/g. A catalyst F is prepared on this substrate by depositing 0.3% by weight of platinum, 0.2% by additional weight of tin so as to obtain 0.4% by weight of tin on the final catalyst, 500 ppm by weight of chlorine and 2% by weight of potassium.

500 cm³ of an aqueous solution of hexachloroplatinic acid and hydrochloric acid is added to 100 g of the alumina substrate that contains tin and indium. It is left in contact for 4 hours, and then it is spin-dried. It is dried at 90° C., and then it is brought into contact with 500 cm³ of an aqueous solution of tin tetrachloride in the presence of hydrochloric acid. It is left in contact for 4 hours, spin-dried, dried at 120° C., and then it is calcined for 2 hours at 500° C. at an air flow rate of 100 liters per hour, with a temperature increase rate of 7° C. per minute. The quantity of tin tetrachloride is selected so as to obtain a total of 0.4% by weight of tin on the calcined product.

The determination of the bimetallicity index and the $H_{ir}$/Pt ratio as well as the dechlorination, the deposition of the potassium, and the final calcination are done as described in Example 1.

EXAMPLE 7

(Invention): Preparation of the Catalyst G
SnInPtSnK/Al2O3

A catalyst G is prepared on the same substrate as in Example 1 by depositing 0.3% by weight of platinum, 0.4% by weight of tin, 0.2% by weight of indium, and 500 ppm by weight of chlorine.

400 cm$^3$ of an aqueous solution that contains tin dichloride is added to 100 g of alumina substrate in the presence of hydrochloric acid. It is left in contact for 4 hours, filtered, dried at 120° C., and then it is calcined for 2 hours at 500° C. at an air flow rate of 100 liters per hour. The quantity of tin dichloride is selected so as to obtain 0.2% by weight of tin on the calcined product. The solid is then brought into contact with 300 cm$^3$ of an aqueous solution that contains indium nitrate in the presence of hydrochloric acid. Again, it is left in contact for 4 hours, spin-dried, and the solid is dried. The solid is then brought into contact with 400 cm$^3$ of an aqueous solution of hexachloroplatinic acid and hydrochloric acid. It is left in contact for 4 hours and then spin-dried. It is dried at 90° C., and then it is brought into contact with 200 cm$^3$ of an aqueous solution that contains tin tetrachloride in the presence of hydrochloric acid. It is left in contact for 4 hours, spin-dried, dried at 120° C., and then it is calcined for 2 hours at 500° C. at an air flow rate of 100 liters per hours, with a temperature increase rate of 7° C. per minute. The quantity of tin tetrachloride is selected so as to obtain 0.4% by weight of tin in all on the calcined product.

The determination of the bimetallicity index and the $H_{ir}$/Pt ratio, as well as the dechlorination, the deposition of the potassium, and the final calcination, are done as described in Example 1.

EXAMPLE 8

Evaluation of the Performance Levels of the Catalysts A to G in Dehydrogenation of n-Dodecane Catalysts A to G are subjected to a test for dehydrogenation of the n-dodecane that is produced in an isothermal tubular reactor. 2 g of catalyst is decreased at 450° C. for 2 hours at a flow rate of 4 liters per hour of hydrogen. The operating conditions are as follows:

Feedstock: n-dodecane

Temperature: 430° C. for 24 hours, then 450° C. for 24 hours and sampling of effluents for analysis, then 470° C. with sampling for analysis after 24 hours, followed by 120 additional hours at 470° C., then 24 hours at 450° C., and sampling for analysis.

Pressure: 0.27 MPa

H2/nCl2 (molar): 5

Mass rate of liquid nCl2/catalyst mass: 50 h$^{-1}$

The results that are obtained after analysis of the various samples under these conditions are reported in Table 1 below. The conversion values of nCl2 and yields are expressed in % by weight relative to the feedstock.

TABLE 1

Characteristics and Performance Levels of Dehydrogenation of n-Dodecane of the Catalysts A to G

| Catalyst | BMI | $H_{ir}$/Pt | Temperature (° C.) | Conversion (%) of n-C12 | Yield (%) of C12 Olefins | Yield (%) of C12 Aromatic Compounds |
|---|---|---|---|---|---|---|
| A (Inv.) | 115 | 0.52 | 450 | 10.0 | 9.3 | 0.2 |
|  |  |  | 470 | 14.7 | 13.3 | 0.5 |
|  |  |  | 450 | 9.3 | 8.5 | 0.1 |
| B (Inv.) | 111 | 0.55 | 450 | 9.9 | 9.2 | 0.2 |
|  |  |  | 470 | 14.5 | 13.0 | 0.6 |
|  |  |  | 450 | 9.2 | 8.4 | 0.1 |
| C (Comp.) | 103 | 0.65 | 450 | 9.9 | 9.1 | 0.3 |
|  |  |  | 470 | 14.1 | 12.3 | 0.7 |
|  |  |  | 450 | 8.5 | 7.7 | 0.1 |
| D (Comp.) | 109 | 0.34 | 450 | 7.8 | 7.2 | 0.2 |
|  |  |  | 470 | 10.9 | 9.6 | 0.5 |
|  |  |  | 450 | 6.8 | 6.1 | 0.1 |
| E (Inv.) | 130 | 0.50 | 450 | 10.1 | 9.5 | 0.1 |
|  |  |  | 470 | 14.8 | 13.6 | 0.4 |
|  |  |  | 450 | 9.8 | 9.1 | 0.1 |
| F (Inv.) | 122 | 0.51 | 450 | 10.0 | 9.3 | 0.2 |
|  |  |  | 470 | 14.8 | 13.4 | 0.6 |
|  |  |  | 450 | 9.6 | 8.8 | 0.1 |
| G (Inv.) | 133 | 0.49 | 450 | 10.1 | 9.4 | 0.2 |
|  |  |  | 470 | 14.9 | 13.6 | 0.5 |
|  |  |  | 450 | 9.9 | 9.2 | 0.1 |

The catalysts A, B, E, F and G that are prepared according to the invention and that have bimetallicity indices of greater than 108 and Hir/Pt ratios of greater than 0.40 lead to olefin yields that are greater than those of the catalysts C and D, catalysts C and D that are prepared according to the prior art. The yield gain of the catalysts according to the invention is obvious in particular during the return to 450° C. after passage to 470°, which reflects a greater catalytic stability of the catalysts according to the invention.

The invention claimed is:

1. A process comprising subjecting a hydrocarbon feedstock to dehydrogenation in the presence of a catalyst that comprises a porous substrate, a noble metal M that is selected from the group consisting of platinum, palladium, rhodium or iridium, at least one promoter X1 that is selected from the group consisting tin, germanium, lead, or an alkali compound, and alkaline-earth compound, in which the X1/M ratio is between 0.3 and 8, the $H_{ir}$/M ratio that is measured by hydrogen adsorption is more than 0.40, and the bimetallicity index BMI that is measured by hydrogen/oxygen titration is more than 108, said catalyst being produced by a process comprising incorporating X1 in two portions, a first portion before introduction of M and a second portion subsequent to introduction of M, wherein the second portion comprises a tetrachloride precursor.

2. The process according to claim 1, in which the catalyst also comprises at least one promoter X2 that is selected from the group of gallium, indium, and thallium, whereby the X2/M ratio is between 0.3 and 8.

3. The process according to claim 1, in which the X1/M atomic ratio is between 0.6 and 6.

4. The process according to claim 2, in which the X2/M ratio is between 0.8 and 4.

5. The process according to claim 1, in which the catalyst comprises only one promoter X1 and in which X1 is tin.

6. The process according to claim 2, in which the catalyst comprises a promoter X1 and a promoter X2 and in which X1 is tin and X2 is indium.

7. The process according to claim 1, in which the catalyst comprises an alkali that is selected from the group of: lithium, sodium, potassium, rubidium and cesium.

8. The process according to claim 1, in which the catalyst comprises lithium or potassium.

9. The process according to claim 1, in which the catalyst comprises an alkaline-earth that is selected from the group: of magnesium, calcium, strontium or barium.

10. The process according to claim 1, in which the catalyst comprises magnesium or calcium.

11. The process according to claim 1, in which the $H_{ir}/M$ ratio of the catalyst is between 0.43 and 0.9.

12. The process according to claim 1, in which the $H_{ir}/M$ ratio of the catalyst is between 0.45 and 0.65.

13. The process according to claim 1, in which the bimetallicity index BMI of the catalyst that is measured by hydrogen/oxygen titration is between 110 and 160.

14. The process according to claim 13, wherein the bimetallicity index is between 115 and 145.

15. The process according to claim 1, wherein the hydrocarbon comprises saturated C8-C16 compounds and the resultant products comprise C8-C16 monoolefins.

* * * * *